United States Patent
Breninger et al.

(10) Patent No.: US 7,016,039 B2
(45) Date of Patent: Mar. 21, 2006

(54) PURGING LIGHT BEAM PATHS IN OPTICAL EQUIPMENT

(75) Inventors: Andrew O. Breninger, Hillsboro, OH (US); Christopher O. Griffiths, Beaverton, OR (US); Douglas C. Mark, Tigard, OR (US); Artemiy Mikheyev, Beaverton, OR (US); Baoliang Wang, Beaverton, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 173 days.

(21) Appl. No.: 10/364,006

(22) Filed: Feb. 10, 2003

(65) Prior Publication Data

US 2004/0156049 A1  Aug. 12, 2004

(51) Int. Cl.
*G01J 4/00* (2006.01)
(52) U.S. Cl. .................. 356/364; 356/365; 356/437; 356/439; 356/440
(58) Field of Classification Search ............... 356/364, 356/365, 432, 436, 437, 438, 439, 440, 244
See application file for complete search history.

(56) References Cited

U.S. PATENT DOCUMENTS

| | | | |
|---|---|---|---|
| 3,895,873 A * | 7/1975 | Dennison et al. ........... 356/312 |
| 3,958,882 A * | 5/1976 | Gast ........................... 356/73 |
| 3,977,786 A * | 8/1976 | Gast ........................... 356/455 |
| 4,413,911 A * | 11/1983 | Rice et al. .................... 356/438 |
| 4,589,775 A * | 5/1986 | Milhous et al. .............. 356/439 |
| 5,499,095 A * | 3/1996 | Gast et al. .................... 356/451 |
| 5,771,260 A * | 6/1998 | Elliott et al. ................. 372/109 |
| 6,268,914 B1 * | 7/2001 | Wang .......................... 356/365 |
| 6,456,361 B1 | 9/2002 | Suzuki et al. |
| 2002/0192579 A1 | 12/2002 | Kamono |
| 2003/0011893 A1 * | 1/2003 | Shiraishi et al. ............ 359/726 |
| 2004/0075834 A1 * | 4/2004 | Kaplan et al. .............. 356/365 |
| 2004/0090628 A1 * | 5/2004 | Ershov et al. ............... 356/438 |

OTHER PUBLICATIONS

Ware, P. Progress Report: 15-nm Lithography Prepares to Graduate, SPIE's oe magazine, Feb. 2003, pp. 14-16.
Mattison D. W., Diode-Laser Sensors for Pulse Detonation Engine Applications, AIAA, Jan. 2002, 5 pages 1-5.

* cited by examiner

*Primary Examiner*—Gregory J. Toatley, Jr.
*Assistant Examiner*—Roy M. Punnoose
(74) *Attorney, Agent, or Firm*—Ipsolon LLP

(57) ABSTRACT

Purging of a light beam path in an effective manner that minimizes the affect of the purging requirement on system throughput. In one embodiment, the invention is incorporated into a birefringence measurement system that has several components for directing light through a sample optical element and thereafter detecting and analyzing the light. The segment of the beam path through the sample is isolated to reduce the volume that requires continual purging.

31 Claims, 2 Drawing Sheets

PURGING LIGHT BEAM PATHS IN OPTICAL EQUIPMENT

TECHNICAL FIELD

This invention relates to purging of contaminants from the path of a light beam, such as a short-wavelength light beam that can be used for photolithography or for measuring the properties of an optical element.

BACKGROUND OF THE INVENTION

The optical lithography industry is currently transitioning to the use of very short exposure wavelengths for the purpose of reducing line weights (conductors, etc.) in integrated circuits, thereby to enhance performance of those circuits. In this regard, the next generation of optical lithography systems will use laser light having a wavelength of about 157 nanometers, which wavelength is often referred to as deep ultraviolet or DUV.

It is important to precisely determine the optical characteristics of the optical elements that are used in systems that employ DUV light. Such an element may be, for example, a calcium fluoride (CaF2) lens of a scanner or stepper. Birefringence is one such characteristic of the optical element.

Birefringence is an intrinsic property of many optical materials, and may also be induced by external forces. The terms retardation or retardance represent the integrated effect of birefringence acting along the path of a light beam traversing a sample optical element. If the incident light beam is linearly polarized with the direction of polarization different from the fast axis of the sample, the two orthogonal components of the polarized light will exit the sample with a phase difference, called the retardance. The unit of retardance can be length, such as nanometers (nm). It is also frequently expressed in units of phase angle (waves, radians, or degrees), which angle is directly proportional to the retardance (nm) divided by the wavelength of the light (nm). A path "average" birefringence for a sample is sometimes computed by dividing the measured retardation magnitude by the thickness of the sample. Oftentimes, the term "birefringence" is interchangeably used with and carries the same meaning as the term "retardance." Thus, unless stated otherwise, those terms are also interchangeably used below.

Since the retardance of an optical element is a characteristic of both the optical material and the wavelength of the light that penetrates the material, a system for measuring retardance properties (hereafter usually referred to as a birefringence measurement system) of an optical element employed in a DUV optical setup must also operate with a DUV light source and associated components in order to precisely detect and process the associated light signals.

There are several problems associated with the use of DUV light in applications such as birefringence measurement or photolithography. One problem concerns absorption of DUV light by oxygen present in the system environment, and in the light beam path in particular. In this regard, the oxygen molecules (as well as other contaminants such as water vapor or trace amounts of hydrocarbons) absorb the DUV light, thus attenuating the light and reducing the signal necessary to make accurate birefringence measurements of the sample.

One way of eliminating the oxygen (as well as other contaminants) in the system environment is to purge the system with nitrogen ($N_2$). Purging, and the maintenance of a purged system, however, will often require reductions in throughput or large, expensive purging systems, especially in instances where a large number of optical components are involved, or the equipment incorporating the optical elements is large.

SUMMARY OF THE INVENTION

The present invention is directed to effective purging of a light beam path, while minimizing the affect of the purging on system throughput.

In one embodiment, the invention is incorporated into a birefringence measurement system that has several components for directing DUV light through a sample and thereafter detecting and analyzing the light. A segment of the beam path, including the path through the sample, is isolated in a chamber to reduce the volume in the equipment that requires continual purging. Moreover, purging gas is directed in a localized or focused manner that maintains a low-oxygen, purged beam path. The chamber is designed to quickly reestablish a purged environment when the chamber is occasionally exposed to ambient oxygen, such as during the loading and unloading of a sample.

Other advantages and features of the present invention will become clear upon study of the following portion of this specification and drawings.

DETAILED DESCRIPTION

Figure 1:
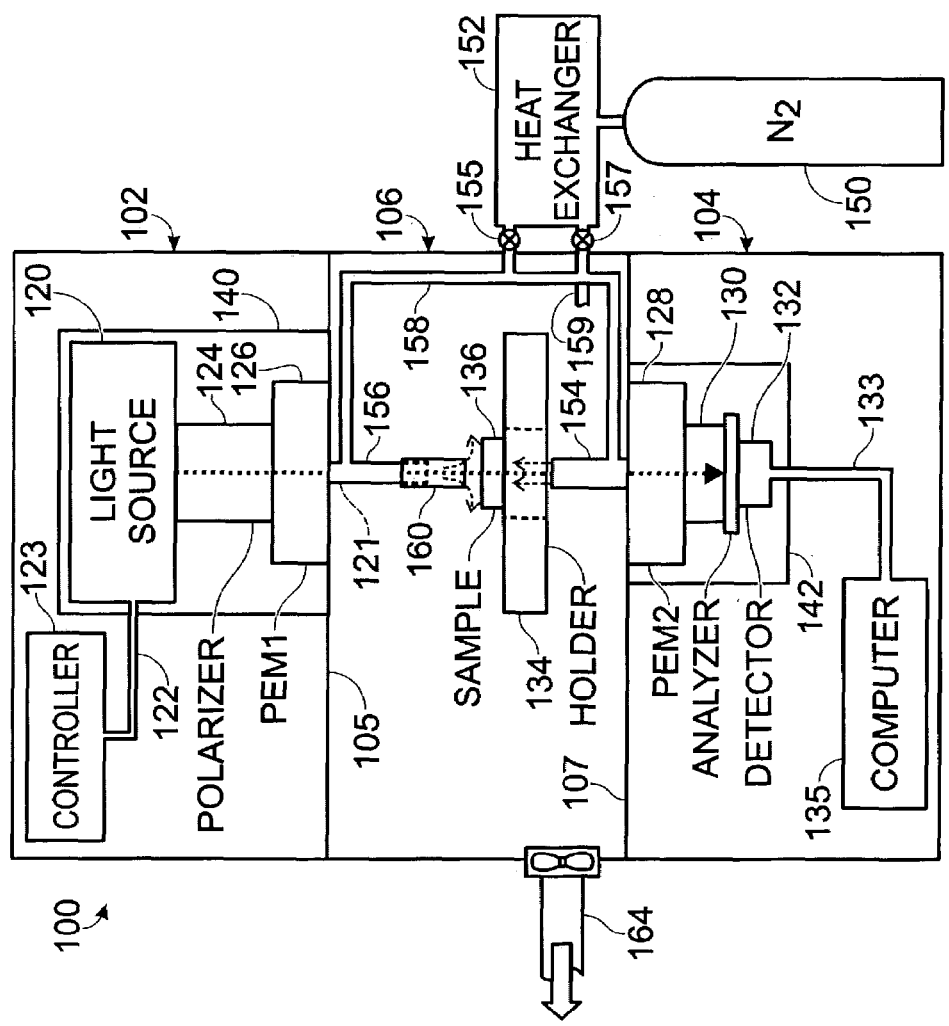
FIG. 1 is a diagram of one preferred system that incorporates the light-beam-path purging of the present invention.

A system that incorporates the light-beam-path purging of the present invention is depicted in FIG. 1. Such a system may be a birefringence measurement system that, as mentioned above, operates with a deep ultraviolet (DUV) light source and associated components for detecting and processing the light signals that are transmitted through a sample optical element.

It is noteworthy here that the birefringence measurement system discussed next is only one of many possible embodiments for the beam path purging system of the present invention, and it is to be kept in mind that the particular components of the birefringence measurement system are described here for illustrating the underlying invention. Also, although the invention is often characterized as beam path purging, it is understood that the environment of the system in an isolated chamber enclosing the sample is also purged.

The birefringence measurement system 100 under consideration is arranged in three primary compartments or modules. An upper module 102, a lower module 104 and a sample module 106.

The upper module 102 includes a DUV light source 120 that can be, for example, a deuterium lamp combined with a monochromator. The lamp irradiates a wide range of wavelengths. The monochromator is set to select the wavelength that is desired for the particular birefringence measurement application (such as 157 nm+/−10 nm). It is contemplated that other lamps, such as mercury lamps and xenon lamps, can be used for birefringence measurements in different spectral regions. In this regard, it is noted that the hereafter described beam path purging features of the present invention are not limited to a beam having a particular wavelength, such as 157 nm, although the importance of effective purging is increased at wavelengths in the DUV portion of the spectrum.

It is also contemplated that a light beam may be generated by a laser source, such as an excimer- or fluorine-type laser.

The light beam 121 emanating from the source 120 is directed through a polarizer 124 and then though a first photoelastic modulator (PEM1) 126 that modulates the polarization of the beam before the beam is directed into the sample module 106 for passage through the sample optical element 136 (hereafter, "sample"). The sample may be, for example, a lens blank for which a retardance characteristic is to be determined. The sample 136 is mounted to a sample holder 134 in a manner that permits passage of the beam 121 through the sample. The holder is a X/Y stage type that is controllable for moving the sample in a translational sense along orthogonal (X and Y) axes so that birefringence data can be collected for a plurality of locations across the surface of the sample. After passing through the sample the beam passes into the lower module 104. The particulars of the lower module 104 are discussed next before returning to the description of the sample module 106 and its contents.

The lower module 104 includes a second photoelastic modulator (PEM2) 128 that modulates the polarization of the beam 121 that emanates from the sample 136. The beam 121 then passes through an analyzer 130 before reaching an adjacent detector 132.

As one aspect of the present invention, the system is constructed and arranged so as to minimize the volume (through which the light beam passes) that must be continually purged of oxygen. The modular arrangement of the system components is convenient for accomplishing this. In particular, the components of the upper module 102 discussed above are sealed in a casing, as depicted at 140 in the FIG. 1 diagram. The casing 140 may be any suitable material, such as metal sheeting, that is constructed to enclose all of the upper module optical components from ambient atmosphere. Control cabling (such as shown at 122) and other connectors passing through the walls of the casing 140 are sealed at the casing wall in a conventional way so that there remains a sealed volume inside the casing.

The upper module 102 may include a cabinet that houses the upper module casing 140 and any related equipment, such as a controller 123 for controlling the light source 120 and the photoelastic modulator 126.

The upper module casing 140 can be a single enclosure or a stack of separate enclosures of each component. The casing(s) 140 is purged of oxygen and sealed from ambient air. Alternatively, the casing 140 may be evacuated. The casing 140 is mounted in airtight fashion to the top wall 105 of the sample module 106 (FIG. 1). The aperture of the photoelastic modulator 126 aligns with an aperture in that wall 105 so that the beam 121 enters the sample module 106 to pass through the sample 136.

Similarly, the components of the lower module 104 discussed above are sealed in a casing, as depicted at 142 in FIG. 1. The casing 142 may be any suitable material, such as metal sheeting, that is constructed to enclose all of the lower module components from ambient atmosphere. Control cabling (such as shown at 133) and other connectors passing through the walls of the casing 142 are sealed at the casing wall in a conventional way.

The lower module 104 includes a cabinet that houses the lower module casing 142 and any related equipment, such as a computer 135 for processing the signal data collected by the detector 132.

The lower module casing 142 can be, like the upper module casing, a single enclosure or a stack of separate enclosures of each component. The casing 142 is purged and sealed from ambient air, and mounted in airtight fashion to the bottom wall 107 of the sample module 106. The aperture of the second photoelastic modulator 128 in the lower module 104 aligns with an aperture in that wall 107 so that the beam 121 propagating through the sample 136 passes into the set of optical components of the lower module 104.

Although the light beam 121 passes through all three modules, the isolated internal chamber defined by the sample module 106 is hermetically sealed from the other two modules of the system. The sample module 106 encloses the sample holder 134 and the sample 136 and can be exposed to oxygen because of the need to provide access to that module (as explained more below) for changing or rearranging a sample. That is, the necessary, occasional access to the interior of the sample module exposes that chamber to oxygen in the atmosphere surrounding the system. Thus, this module 106 receives the local or focused purging mentioned above. One can appreciate that by isolating the sample module 106, only a relatively small volume of the overall optical system (that is, the system including all of the optical elements through which the light beam passes) will require continual purging.

One preferred mechanism for purging includes a supply of nitrogen 150, which can be stored in liquid form. The liquid nitrogen is expanded to a gaseous state and heated to ambient temperature via a temperature controlled heat exchanger 152 that is interconnected between the supply 150 and the sample module 106. Other gases, such as helium, could be used instead of nitrogen. The heat exchanger 152 is housed in a compartment that is thermally isolated from the sample module 106.

The focused application of the purging gas includes a pair of gas delivery tubes 154, 156 that are pressurized with purging gas that is provided by bifurcated tubing 158 that conducts the gas from the heat exchanger 152 to the interior of each tube 154, 156. Gas flow to the tubing 158 is controlled by an electronic valve 155 that, under control of the computer 135, can be closed whenever the beam is not in use.

The upper tube 156 is mounted to the wall 105 of the sample module 106 in a manner such that it is axially aligned with the light beam 121. Thus, after the beam 121 exits the sealed, upper-module casing 140 it propagates through the nitrogen-saturated interior of the tube 156 to the sample 136.

It is noteworthy here that the light source 120, which generates a significant amount of heat during use, is thermally isolated from the sample chamber 106, including the tubing that delivers purging gas within the sample chamber. The compartmented temperature-controlled heat exchanger 152 is also thermally isolated from the light source as well as the sample chamber. As a result of this thermal isolation, the temperature of the purging gas delivered to the sample remains stable so that no temperature gradients are induced in sample, which gradients could vary the optical characteristics of the sample.

Preferably, the upper tube 156 has a telescopic extension 160. The extension 160 can be retracted to provide clearance for easily replacing the sample 136, and extended once the sample is in place on the holder 134 so that the open end of the tube extension 160 is adjacent to the upper surface of the sample. The gas pressure supplied to the tubes is selected so that the purging gas exiting the tube extension 160 provides a positive pressure in the gap that resides between the tube and the sample surface, thereby preventing the entry of oxygen into this otherwise exposed segment of the beam path.

The lower purge-gas delivery tube 154 is mounted to the bottom wall 107 of the sample module 106 so that it is axially aligned with the beam 121. Thus, after the beam 121 propagates through the sample 136, it passes through the interior of the tube 154 and to the lower module casing 142 as described above. Accordingly, the beam 121 propagates through the nitrogen-saturated interior of the tube 154 in the path to the lower module 104.

Preferably, the open end of the lower tube 154 extends to be adjacent to the undersurface of the sample holder 134 (hence, adjacent to the sample). The pressure of the purging gas is selected so that the gas exiting the tube 154 provides a positive pressure in the gap between the tube and the sample undersurface, thereby preventing the entry of oxygen into this segment of the beam path.

It is contemplated that a single, focused gas delivery tube will suffice, with or without a telescopic extension. Also, in some birefringence measurement systems, the beam is completely or partly reflected from the sample toward a separate set of detection components. It will be clear to one of ordinary skill that the present invention can be used with such a system by sealingly enclosing those other components (such as by a casing similar to the ones 140, 142 discussed above) and arranging another purging gas delivery tube in axial alignment with the reflected light beam.

It is also contemplated that the gas purging tubes could be sized and arranged with axes perpendicular to that of the beam, thereby to direct the purging gas across the beam path in instances where it might not be desirable or possible to have the light beam pass through the interior of the tubes.

Although the purging gas is focused where its presence is most important, along the path of the light beam, it is noted that the entire interior chamber of the sample module 106 is purged of oxygen. To this end, one preferred embodiment of the present invention includes additional or secondary purging gas delivery, as by a separate port 159 fed from the heated source of nitrogen and controlled by a computer controlled electronic valve 157. The provision of the secondary purging permits a dual or staged approach to purging. For example, the secondary purging (via port 159) may be applied substantially continuously during operation of the system 100, thereby maintaining a very low concentration of oxygen in the supply chamber. For efficient use of the purging gas, the primary or focused gas purging (via delivery tubes 154, 156) may be used only at times when the light beam is directed through the sample chamber.

It is noted that even though only a single port 159 and valve 157 are depicted, it will be understood that several such ports and valves could be used for effective secondary purging described here.

An exhaust vent 164 is provided, with or without an associated fan, with a one-way flap or check valve to prevent exhausted gas from returning from the vent to the chamber of the sample module 106.

Figure 2:
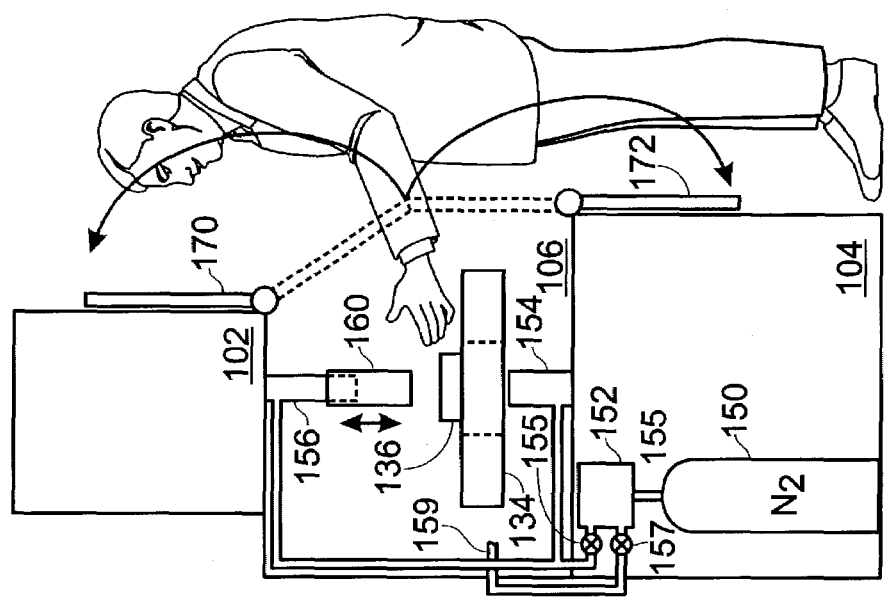
FIG. 2 is a somewhat schematized side view of the system diagrammed in FIG. 1.

FIG. 2 shows how, in a preferred embodiment, the sample module 106 may be accessed by an operator through hinged doors 170, 172 that, when closed, seal the chamber of that module. As mentioned, such access to the module may introduce unwanted oxygen into the sample module 106. In any event, since the volume of the sample module is relatively small, owing to its isolation from the remaining modules of the optical system, an adequately purged chamber within the sealed sample module can be rapidly reestablished after the module doors 170, 172 are again closed. The beam path through the sample module 106 is immediately purged owing to the effect of the purging gas delivery (tubes 154, 156 and port 159) discussed above.

It is contemplated that the secondary purging provided via the above-discussed port 159 (or any similar secondary purging-gas delivery system) may be optional. That is, in instances where the interior chamber of the sample module 106 is configured with as small a volume as practical, and where that chamber is carefully isolated (including well-sealed access doors), the focused, delivery of gas, such as via tubes 154, 156, will suffice for maintaining a tolerably low oxygen concentration in the sample chamber.

It is also pointed out that because the sample module 106 is equipped with a minimum amount of components, contamination sources from those components (such as by material disintegration or out-gassing) are similarly minimized.

In some imaging optical systems, including optical lithographic step-and-scan systems, calcium fluoride lenses are typically used to bend the light rays in order to achieve certain numerical apertures. Therefore, it is important to study the angular dependence of birefringence in calcium fluoride samples relative to the incident light beam. One way to analyze this angular dependence is to orient the surface of the optical sample at an inclined or tilted orientation to establish the desired angle of incidence for the beam.

Figure 3:
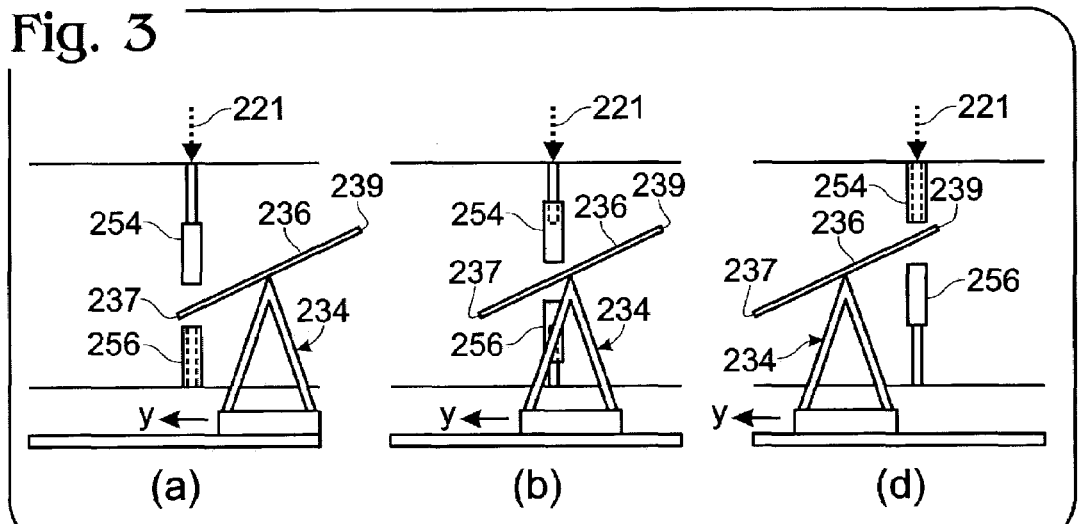
FIG. 3 is a three-part diagram showing an embodiment of the invention wherein a sample optical element that is held in an inclined or tilted orientation is moved relative to the beam path.

The diagram of FIG. 3 schematically illustrates an example of how a tilted optical element sample 236 may be traversed (here in a linear, "Y," direction) across the fixed path of a light beam 221 in a system that is otherwise comparable to the birefringence measurement system 100 discussed above (isolated, purged sample chamber, etc.). The sample 136 is incrementally traversed by the X/Y stage sample holder 234 so that birefringence data can be collected over a plurality of locations across the surface of the sample.

It will be appreciated that as a result of the movement of the tilted sample 136 relative to the light beam 221 there will occur a change in the distance between the sample surface and the ends of purging gas delivery tubes that surround the beam. As an aspect of the present invention, there is provided a purging gas delivery system that is adjustable to account for the movement of a tilted sample relative to the light beam and that also maintains the gas purging tubing such that the tubing opens adjacent to the surface of the sample. This embodiment is illustrated in FIGS. 3 and 4 and discussed next.

FIG. 3(a) illustrates one position of the tilted sample 236 relative to the light beam 221 where a relatively low leading edge 237 of the sample crosses the path of the beam 221. In this embodiment, a telescopic, upper purging-gas delivery tube 256 is provided as shown schematically in FIG. 3 and in FIG. 4. Beneath the sample, there is a similar telescopic, lower purging-as delivery tube 254.

In the sequence of drawings FIGS. 3(a)–3(c) it is shown how the upper gas deliver tube 256 is retracted and the lower gas delivery tube 254 extended as the sample 236 is traversed from left to right in the figure. From that figure, it can be appreciated that the ends of the purging gas tubes are maintained in close proximity to the surfaces of the sample, thereby ensuring that the gap that resides between the tube and the sample remains under positive pressure from the purging gas that flows from the tubes.

Figure 4:
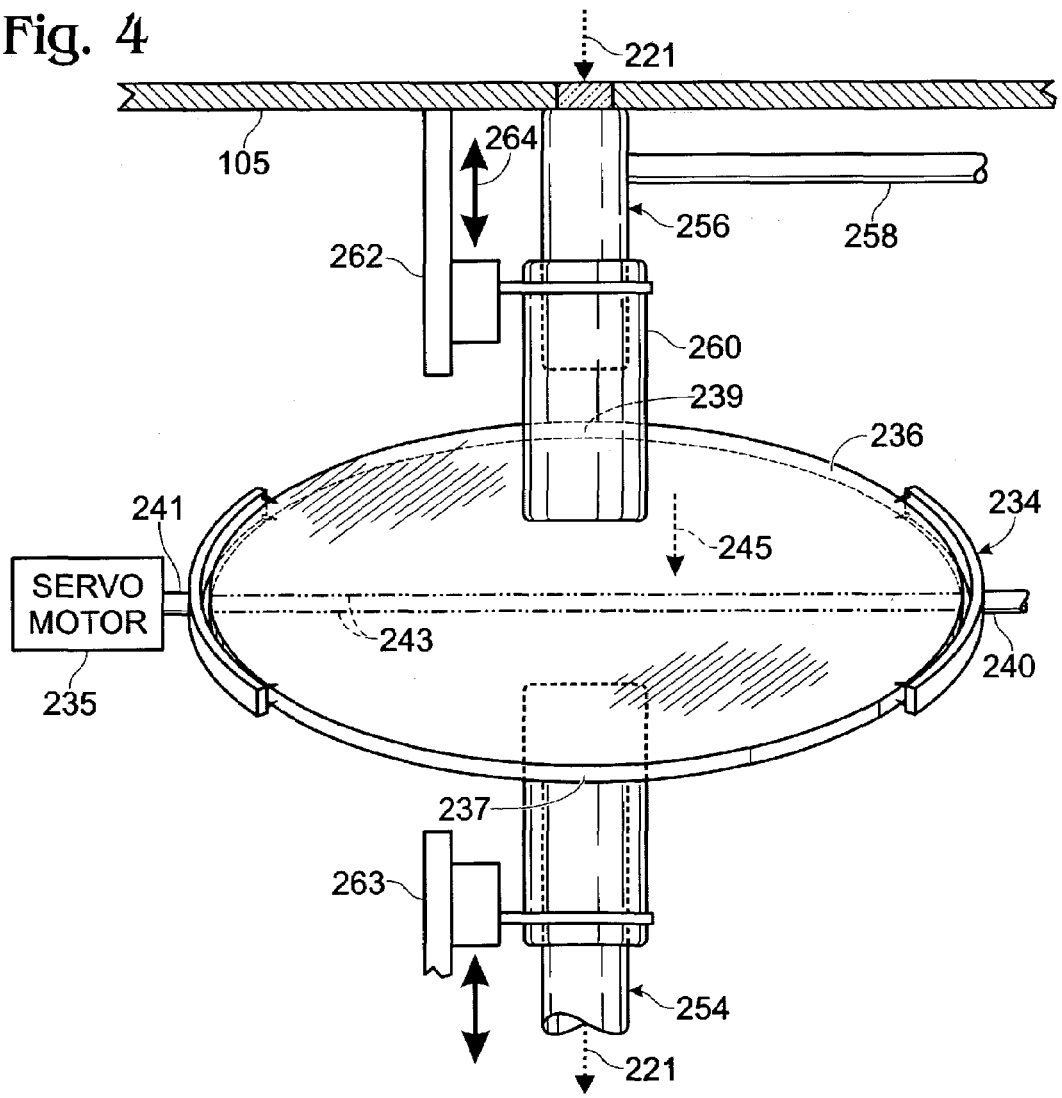
FIG. 4 is an enlarged detail diagram of the embodiment of FIG. 3 illustrating movement of purging gas delivery tubes relative to a movable, tilted sample.

With reference to FIG. 4, the adjustable purging-gas tubes 256 and 254 can be configured in any of a number of ways. In one embodiment, the telescopic upper tube 256 is mounted to the top wall 105 of the sample module and supplied with purging gas through one branch of by bifurcated tubing 258 that corresponds to the tubing 158 described above.

An extension part 260 of the upper tube 256 is connected to a linear actuator 262 that is mounted adjacent to the tube 256. The actuator 262, under the control of the computer 135, is operable to extend and retract the connected extension part 260 in the opposing directions shown by arrow 264 in FIG. 4. The lower, telescopic tube 254 is similarly extended and retraced by a computer controlled linear actuator 263.

The sample holder 234 may be constructed to hold the sample 236 in a particular angle relative to the incident light beam 221. In such an instance, the computer 135 is programmed with information that correlates the Y-position of the sample holder with the position of the sample surfaces so that the linear actuators may be controlled to maintain the ends of the tubes 256, 254 in close proximity with the respective surfaces of the sample as the sample is traversed. For example, with reference to FIG. 3, the linear actuators are controlled to incrementally retract the upper tube 254 and extend the lower tube 256 as the sample is traversed from left to right in that figure.

The tubes are retractable by an amount sufficient to ensure (in this embodiment) there is no contact between the lower tube and the leading end 237 of the sample, or between the upper tube 254 and the trailing end 239 of the sample.

It is also contemplated that the sample holder 234 may be designed to rotate the sample to facilitate, for example, analysis of the sample's birefringence properties at a number of different angles of incidence to the light beam. For example, the holder 234 shown in FIG. 4 secures the sample 236 about aligned pivot posts 240 241. A servomotor 235 is connected to one post or shaft 241 and operable by the computer for rotating the sample to the desired angle for analysis. In one embodiment, the servomotor is provided with an encoder that provides shaft 241 position information to the computer. The position information is processed to determine the relative positioning of the sample surfaces, and the lengths of the purging gas tubes 254, 256 are timely adjusted (via the linear actuators 262, 263) to maintain the respective tube ends in close proximity with the sample surfaces, as discussed above.

For example, the servo motor 235 can be driven to rotate the sample 236 from the angled orientation shown in solid lines in FIG. 4 to a horizontal position as shown by dashed lines 243. The upper tube is thus extended in the direction shown by arrow 245 until the end of that tube is adjacent the sample surface. The lower tube 254 is correspondingly retracted.

Although preferred and alternative embodiments of the present invention have been described, it will be appreciated that the spirit and scope of the invention is not limited to those embodiments, but extend to the various modifications and equivalents as defined in the appended claims.

What is claimed is:

1. An apparatus for projecting a light beam through an optical element to a detector, comprising:
   a first module including a source for the light beam;
   a second module including the detector;
   a sample module between the first and second modules, the sample module having a chamber that is hermetically isolated from the first and second modules;
   a holder for the optical element, the holder located in the chamber; and
   purging means for removing contaminants from the chamber including two tubes, each tube having an end that extends inside the chamber, the tubes being arranged so that the holder is between those ends.

2. The apparatus of claim 1 wherein the end of at least one tube is telescopically extendable inside the chamber.

3. The apparatus of claim 1 wherein the tubes are supplied with a substantially inert gas, the purging means also including exhaust means for exhausting the chamber of the sample module.

4. The apparatus of claim 3 wherein the gas is nitrogen.

5. The apparatus of claim 1 further comprising a sealable access door mounted to the sample module and permitting access to the chamber when the door is open.

6. The apparatus of claim 5 wherein the door is arranged so that when open the chamber of the sample module remains isolated from the first and second modules.

7. The apparatus of claim 1 wherein the source provides light having a wavelength of about 157 nm.

8. The apparatus of claim 1 including:
   stage means for securing an optical element in the holder and moving the holder relative to the tubes; and
   adjustment means for changing the length of the ends of both tubes within the chamber and in relation to the movement of the holder.

9. The apparatus of claim 8 wherein the stage means is a mechanism for securing the optical element in a tilted orientation relative to the light beam.

10. The apparatus of claim 1 including secondary purging means for delivering purging gas to the chamber in addition to that delivered by the gas delivery tube.

11. The apparatus of claim 10 further comprising control means for independently controlling the supply of purging gas in the gas delivery tube and the supply of purging gas delivered by the secondary purging means.

12. An apparatus for projecting a light beam through an optical element to a detector, comprising:
   a first module including a source for the light beam;
   a second module including the detector;
   a sample module between the first and second modules, the sample module having a chamber that is isolated from the first and second modules;
   a holder for the optical element, the holder located in the chamber; and
   purging means for removing contaminants from the chamber, wherein the purging means includes a gas delivery tube connected to a supply of purging gas and having an open end located adjacent to the holder so that gas in the tube is directed therefrom to a part of the holder through which the beam passes; and
   wherein the tube is aligned with the light beam so that the beam passes through the tube.

13. An apparatus for projecting a light beam through an optical element to a detector, comprising:
   a first module including a source for the light beam;
   a second module including the detector;
   a sample module between the first and second modules, the sample module having a chamber that is isolated from the first and second modules;
   a holder for the optical element, the holder located in the chamber; and purging means for removing contaminants from the chamber, wherein the purging means includes a pair of tubes inside the chamber and arranged with one tube located on each of two opposing sides of the holder, wherein the tubes are aligned so that the beam will pass through both tubes; and gas delivery means for directing gas through the tubes toward the two opposing sides of the holder.

14. A method of purging the path of a light beam in the vicinity of a sample holder through which the beam passes, wherein the light beam is part of an optical setup that has a number of optical elements, including a light source, the sample holder, and a detector, the method comprising the steps of:

locating the sample holder in a chamber that is hermetically isolated from the other optical elements, whereby the separated elements are sealed in enclosures that are separate from the chamber; and directing purging gas into the chamber by arranging tubular members on opposing sides of the sample holder and directing the purging gas into the tubular members so that the beam path through the chamber is filled with the gas.

15. The method of claim 14 wherein at least one of the tubular members has an end extension inside the chamber, the method including the step of adjusting the length of the end extension.

16. The method of claim 14 including the step of thermally isolating the light source from purging gas that is directed to the chamber.

17. The method of claim 16 including the step of thermally isolating a source of the purging gas from the chamber.

18. The method of claim 16 further comprising source heating means for heating a source in a compartment that is isolated from the chamber and from the light source.

19. A method of purging the path of a light beam in the vicinity of a sample holder through which the beam passes, wherein the light beam is part of an optical setup that has a number of optical elements, including a light source, the sample holder, and a detector, the method comprising the steps of:

locating the sample holder in a chamber that is isolated from the other optical elements, whereby the separated elements are sealed in enclosures that are separate from the chamber; and directing purging gas into the chamber, wherein the directing step includes locating a tubular member in the chamber so that the gas and the light beam pass through the tubular member.

20. An assembly for analyzing optical properties of a sample, comprising:

a first module including a first set of optical elements for providing a source of light and for modulating the polarization of the light that is then directed through the sample;

a second module including a second set of optical elements for modulating the polarization of the light and detecting a characteristic of the light after that light passes through the sample;

a sample chamber for holding the sample, the chamber being sealed from the first and second modules; and a purging system for purging the atmosphere inside the chamber.

21. The assembly of claim 20 wherein the purging system includes at least one tube through which purging gas is directed toward the sample.

22. The assembly of claim 21 wherein the tube is telescopic.

23. The assembly of claim 21 wherein the purging system also includes a second tube through which purging gas is directed toward the sample, the tubes being aligned so that the light beam passes therethrough.

24. The assembly of claim 20 wherein the first and second set of optical elements are suitable for determining a birefringence characteristic of the sample.

25. The assembly of claim 20 further comprising means for thermally isolating the light source from the sample chamber.

26. The assembly of claim 20 further comprising a gas heating compartment near but thermally isolated from the light source and the sample chamber.

27. A method of directing a light beam through an optical element, comprising the steps of:

locating the optical element in a chamber;

directing purging gas through a tube that has an open end that is adjacent to the optical element;

exhausting the chamber; and aligning the tube with the light beam so that the beam passes through the tube.

28. The method of claim 27 further comprising the step of directing purging gas through a second tube that has an open end that is adjacent to the optical element.

29. The method of claim 28 including the step of arranging the tubes so that each opens to an opposite side of the optical element and so that both tubes are aligned with the beam of light.

30. The method of claim 29 including the step of directing secondary purging gas into the chamber and independently controlling the supply of purging gas in the tube and the supply of secondary purging gas.

31. The method of claim 27 including the step of adjusting the length of the tube in the vicinity of the optical element to locate the open end of the tube at a selected position relative to the optical element, depending upon the size of the optical element.

* * * * *